United States Patent [19]

Sugarbaker

[11] Patent Number: 5,342,384
[45] Date of Patent: Aug. 30, 1994

[54] SURGICAL DILATOR

[75] Inventor: David J. Sugarbaker, Brookline, Mass.

[73] Assignee: Brigham & Women's Hospital, Boston, Mass.

[21] Appl. No.: 929,311

[22] Filed: Aug. 13, 1992

[51] Int. Cl.⁵ .......................................... A61M 29/00
[52] U.S. Cl. ................................... 606/191; 604/104
[58] Field of Search ................ 604/43, 104; 606/190, 606/191, 197, 198, 222, 223, 108

[56] References Cited

U.S. PATENT DOCUMENTS

| | | | |
|---|---|---|---|
| 586,776 | 7/1897 | Lewis | 606/191 |
| 3,196,876 | 5/1961 | Miller | |
| 3,938,504 | 2/1976 | Dickinson, III et al. | |
| 4,013,079 | 3/1977 | Lindemann et al. | |
| 4,263,914 | 4/1981 | Pawlak | 606/197 |
| 4,328,811 | 5/1982 | Fogarty | |
| 4,449,532 | 5/1984 | Storz | |
| 4,686,984 | 8/1987 | Bonnet | |
| 4,726,373 | 3/1988 | Greengrass | |
| 4,862,891 | 9/1989 | Smith | |
| 5,030,227 | 7/1991 | Rosenbluth et al. | |

OTHER PUBLICATIONS

Abstract-Storz, DE3337-758, German patent.

*Primary Examiner*—C. Fred Rosenbaum
*Assistant Examiner*—N. Kent Gring
*Attorney, Agent, or Firm*—Hamilton, Brook, Smith & Reynolds

[57] ABSTRACT

A medical dilator for stretching an incision having a smooth convex tip and wherein the rod has at least one cross sectional area which is oval to induce more stretching in a first direction than in a direction normal to the first direction.

15 Claims, 3 Drawing Sheets

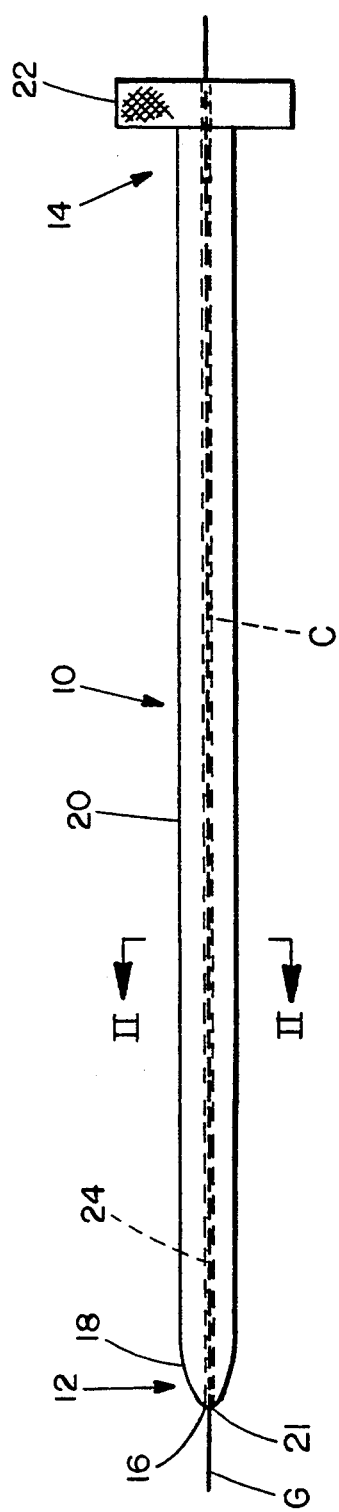
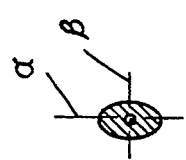
FIG. 1
FIG. 2
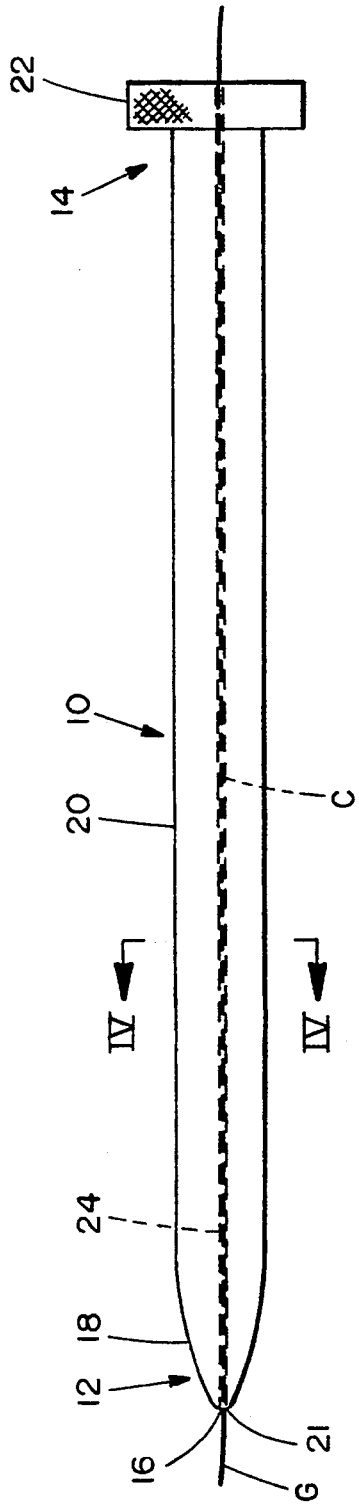
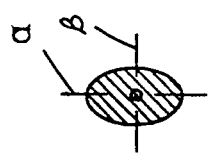
FIG. 3
FIG. 4

5,342,384

SURGICAL DILATOR

BACKGROUND OF THE INVENTION

Endoscopic surgery, or what is also called video surgery, employs an external miniaturized video camera attached by fiber optic tubes to a light source and a telescopic lens, both of which are inserted as a unit through a small incision made in a patient's body. The camera projects on to a video screen a picture of the surgical field illuminated by the light source and taken totally within the body. Other surgical instruments, such as scalpels, retractors and the like, which are specially designed for endoscopic surgery are inserted through one or more additional incisions in the patient. As a result, the surgeon does not view the operative field itself, but rather, views the picture on the video screen while performing the surgery.

The benefits derived from this type of surgery are numerous. The process, in some forms, is almost bloodless. Large ugly scars are eliminated. The process is much less traumatic and painful to the patient than open surgery. The patient leaves the hospital in a few days, and often the same day as with some endoscopic procedures in the joints called arthroscopic surgery.

When endoscopic surgery is performed in the chest cavity or thorax, the technique is called thoracoscopic surgery. Quite frequently, the endoscope including the light source and telescopic lens are inserted through small incisions made between the ribs through the intercostal muscle. As indicated above, one or more additional incisions are often made to admit other instruments into the thoracic cavity such as scalpels, retractors and the like.

The displacement of a rib is extremely painful, particularly if it is displaced from the sternum to which it is joined. It has often been said in the vernacular "It is less painful to break a rib than to displace one."

Since thoracic surgery is conveniently performed by inserting the endoscope lens and light source through incisions between the ribs, extreme care must be taken not to displace or separate one rib from another. Various options are open to the surgeon. One is to make a relatively large incision in the intercostal muscle between two adjacent ribs sufficient to admit the scope or the surgical instrument. This results in excessive bleeding, extensive suturing and a longer time to heal than a small incision, which is to be avoided.

Another option is to make a relatively small incision in the muscle and then enlarge the aperture by stretching the muscle rather than cutting it. If this were done transversely of the adjacent ribs, excessive pressure could cause the ribs to be displaced resulting in extreme pain to the patient which could last for days.

It is to this general problem that the present invention is directed.

SUMMARY OF THE INVENTION

The invention resides in a medical dilator for stretching an incision in muscle or tissue which includes a rod having a distal end, a proximal end and a smooth convex tip at the distal end. The tip is continuous with a portion of the rod of progressively increasing girth which leads to an intermediate portion.

There is at least one cross sectional area of the rod which is oval to induce more stretching in a first direction than in a direction normal to the first direction.

The rod has a central axis with a continuous open passageway passing from the distal end to the proximal end to accommodate a guidewire.

A gripping portion is located at the proximal end through which the continuous passageway extends.

In one embodiment, the rod may be hollow from end to end with an opening at the tip and an opening at the proximal end.

In another embodiment of the invention, the rod may be solid with a central passageway extending from end to end.

When the rod is hollow from end to end, an interior conical guideway may be located within the rod in the gripping portion to facilitate the exit of a guidewire along which the rod passes in the inserting process.

In still another embodiment of the invention, the rod is hollow and has a tube located within it from the tip extending to the proximal end and out through the gripping portion to accommodate the guidewire.

The above and other features of the invention including various and novel details of construction and combination of parts will now be more particularly described with reference to the accompanying drawings and pointed out in the claims. It will be understood that the particular surgical dilator embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 1 is a side view of a surgical dilator embodying the invention.

FIG. 2 is a sectional view taken along the lines II—II on FIG. 1.

FIG. 3 is a view similar to FIG. 1 of the surgical dilator but showing a dilator of larger size.

FIG. 4 is a sectional view taken along the line IV—IV in FIG. 1.

DETAILED DESCRIPTION

The invention resides in a medical dilator for stretching an incision in muscle or tissue. Dilators of the type herein disclosed come in sets of progressively increasing girth and are used sequentially. The smallest of the set is inserted in a very small incision in the skin and adjacent tissues of a patient. The first dilator stretches the tissue and each dilator successively stretches the tissue further until the desired opening is obtained. The appropriate surgical instrument or liner is inserted in the dilated incision and upon completion of the operation, the skin and tissue return to their normal size requiring only one or more sutures to close the incision.

Figure 5:
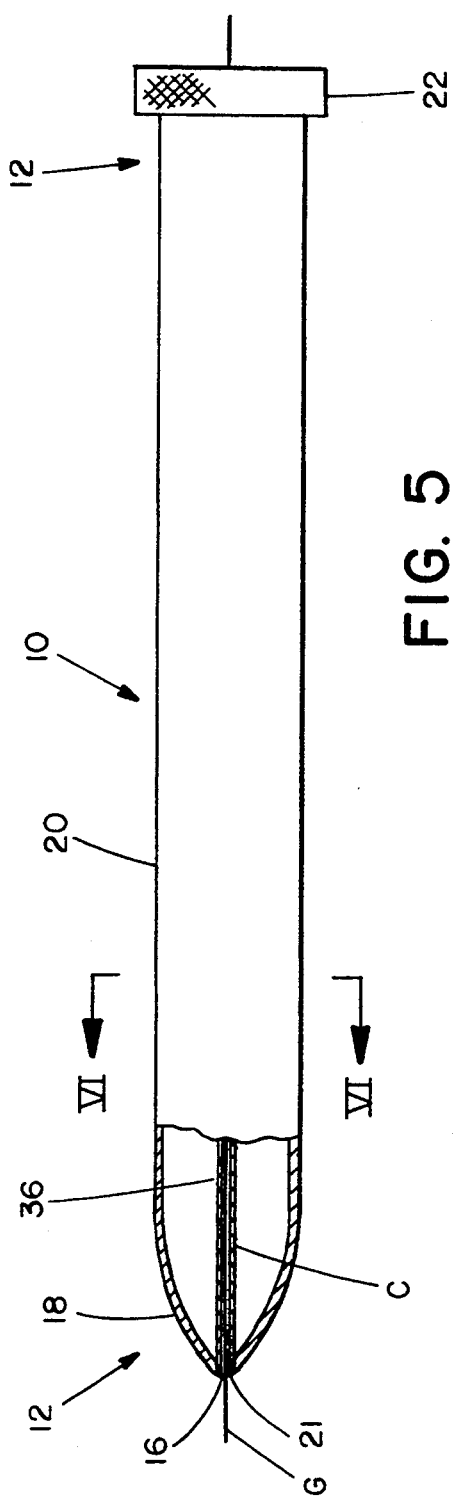
FIG. 5 is a side view of a still larger dilator embodying the invention with a portion broken away for clarity.

A series of such dilators is seen in FIGS. 1, 3 and 5. Each of the dilators 10 is in the form of a rod having a distal end 12 and a proximal end 14. A smooth convex tip 16 is located at the distal end and is continuous with a portion 18 of the rod of progressively increasing girth which leads to an intermediate portion 20. A hole is formed in the tip 16.

At the proximal end of the rod is a gripping portion 22 in the form of a knurled disk of slightly larger girth than that of the dilator itself.

As will be seen in sectional views 2, 4 and 6, there is at least one area of the intermediate portion 20 of the rod having an oval cross section. While it is only necessary to have one area formed as an oval, for the convenience of manufacture, the entire length of the intermediate portion 20 is oval as is that of portion 18. As will be seen best in FIG. 6, the oval has a major axis α and a minor axis β. Each of the dilators has a central axis C.

Figure 8:
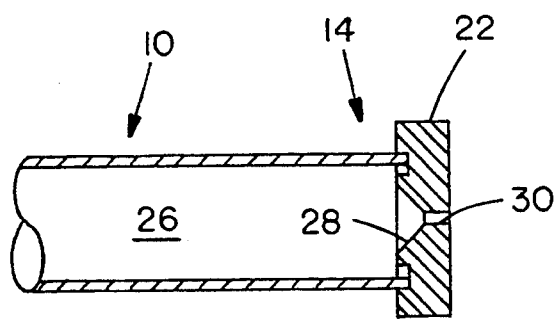
FIGS. 8, 9 and 10 are fragmented sectional views of the dilator showing three embodiments of its internal construction.
Figure 9:
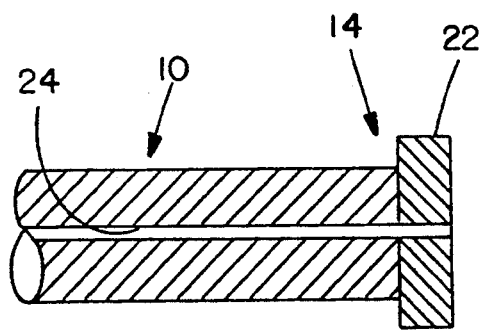

The dilators shown in FIGS. 1 and 3 are solid in cross section as seen best in FIGS. 2 and 4 and include a central passageway 24. In this instance, the passageway 24, best seen in FIG. 9, is continuous and open from the hole 21 in the tip 16 to the proximal end 14, passing through the gripping portion 22. Another embodiment of construction will be seen in FIGS. 6, 8 and 10 wherein the entire dilator rod is hollow as designated at 26.

In operation, the guidewire G may be inserted first in the incision and then the dilator 10 is slid along the guidewire which enters the hole 21 or may be inserted along with the first dilator, i.e., the one with the smallest girth. The guidewire remains in the incision when the dilator is removed and the successive dilators are slid over the wire. The guidewire then passes through the opening 24 or through the hollow interior 26 as it enters the incision.

In order to assure that the guidewire G emerges from the dilator, the inner rear portion of the gripping portion 22 may be provided with a conical guideway 28 (FIG. 8) leading to a passageway 30.

Where the rod is solid, as seen in FIG. 9, the passageway 24 will extend outwardly of the end of the gripping portion 22.

Figure 6:
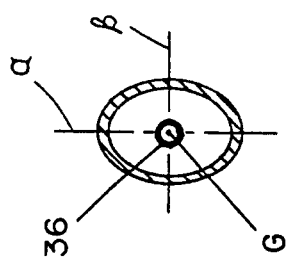
FIG. 6 is a sectional view taken along the line VI—VI on FIG. 5.
Figure 10:
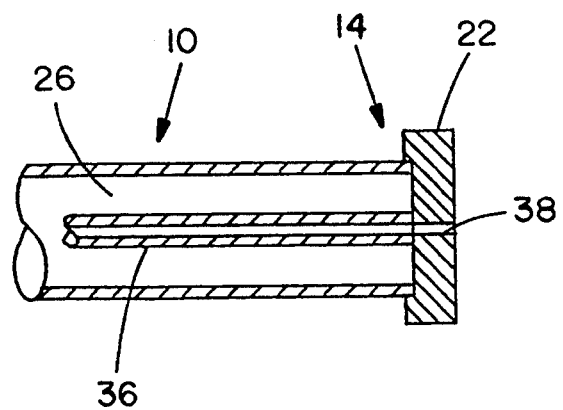

Another configuration of construction will be seen in FIGS. 6 and 10. In this configuration, the dilator 26 is hollow as at 26. A tube 36 is located in the passageway extending from the opening 21 in the tip 16 and leading out through an opening 38 in the rear end of the gripping portion 22.

Figure 7:
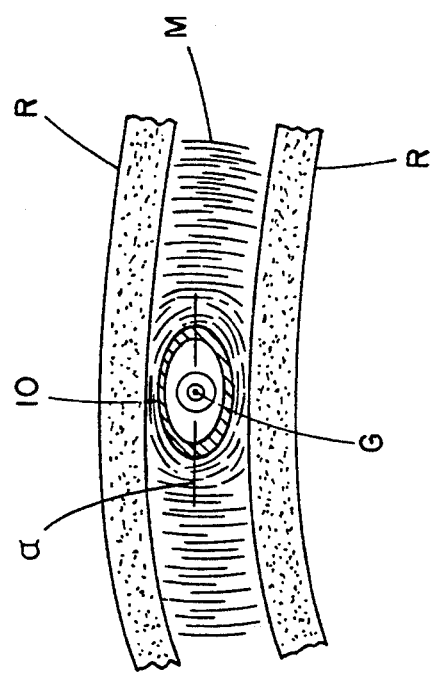
FIG. 7 is a schematic view of one dilator of the series inserted in intercostal muscle between two adjacent ribs.

Thoracic surgery is now being performed quite satisfactorily with endoscopes. As will be seen in FIG. 7, which is a schematic showing of a dilator located between ribs R, the surgeon makes a small incision in the skin and the intercostal muscle M which is located between the ribs. In order not to displace the ribs, the surgeon orients the rod with the major axis α of the oval dilator, essentially parallel to the ribs R, such that most of the stretching of the intercostal muscle M takes place lengthwise of the ribs as distinguished from transversely thereto. This prohibits undue pressure being placed on the ribs which would otherwise tend to spread the ribs apart which is to be avoided.

After utilizing the smallest of the dilators, it is removed but the guidewire G remains in the incision. The next larger dilator is than fed along the guidewire also stretching the major axis essentially parallel to the ribs as with the initial dilator. This is done with successively larger oval dilators until the desired size of aperture is obtained.

I claim:

1. In a medical dilator for stretching an incision in muscle or tissue including a rod having a distal end, a proximal end, and
   a central axis extending from the proximal end to the distal end,
   a smooth convex tip being located at the distal end continuous with a portion of the rod of progressively increasing girth leading to an intermediate portion, the intermediate portion having the largest girth along the rod,
   the cross sectional area of the intermediate of the rod being oval and having a major and a minor axis at right angles with the central axis and with each other to induce more stretching in the direction of the major axis than in the direction of the minor axis and the dimensions of the minor axis and the major axis being constant measured along the length of the intermediate portion.

2. In a dilator for stretching an incision in intercostal muscle and surrounding tissue including a rod having a central axis, a distal end, a proximal end and a smooth convex tip at the distal end continuous with a portion of the rod of progressively increasing girth leading to an intermediate portion, the intermediate portion having the largest girth along the rod,
   the cross section of the rod normal to the central axis at all points along the intermediate portion of the rod being oval and having a major axis and a minor axis normal to the central axis to induce more stretching in the direction of the major axis than in the direction of the minor axis, and the dimensions of the minor axis and the major axis being constant measured along the length of the intermediate portion.

3. A thoracic dilator for stretching intercostal muscle and surrounding tissue between ribs comprising:
   a rod having a central axis, a distal end, a distal end, a proximal end, an intermediate portion between ends;
   a smooth convex tip of the distal end continuous with a portion of the rod of progressively increasing girth leading to the intermediate portion;
   a gripping portion at the proximal end;
   a continuous open passageway extending from the convex tip through the gripping portion; and
   the intermediate portion of the rod having an oval cross section having a major axis and a minor axis at right angles to the central axis to induce more stretching of the intercostal muscle along the major axis than in a direction along the minor axis, and the dimensions of the minor axis and the major axis being constant measured along the length of the intermediate portion.

4. A dilator according to claim 1 wherein the rod is hollow from end to end.

5. A dilator according to claim 2 wherein the rod is hollow from end to end.

6. A dilator according to claim 3 wherein the rod is hollow from end to end.

7. A dilator according to claim 1 wherein the rod is solid with a central passageway extending from end to end.

8. A dilator according to claim 2 wherein the rod is solid with a central passageway extending from end to end.

9. A dilator according to claim 3 wherein the rod is solid and with the continuous open passageway passing through it.

10. A dilator according to claim 1 wherein the rod is hollow from end to end, a hole is formed through the center of the convex tip, a second hole being formed through the center of the proximal end and a conical guide is located within the rod at the proximal end leading to the second hole.

11. A dilator according to claim 2 wherein the rod is hollow from end to end, a hole is formed through the center of the convex tip, a second hole being formed through the center of the proximal end and a conical guide is located within the rod at the proximal end leading to the second hole.

12. A dilator according to claim 3 wherein the rod is hollow from end to end, a hole is formed through the center of the convex tip, a second hole being formed through the center of the proximal end and a conical guide is located within the rod at the proximal end through the gripping portion leading to the second hole.

13. A dilator according to claim 1 wherein the rod is hollow and a tube is located within the rod forming a continuous open passageway from end to end.

14. A dilator according to claim 2 wherein the rod is hollow and a tube is located within the rod forming a continuous open passageway from end to end.

15. A dilator according to claim 3 wherein the rod is hollow and a tube is located within the rod forming a continuous open passageway from end to end.

* * * * *